(12) United States Patent
Orwar et al.

(10) Patent No.: US 7,018,819 B2
(45) Date of Patent: Mar. 28, 2006

(54) METHOD AND APPARATUS FOR MANIPULATION OF CELLS AND CELL-LIKE STRUCTURES FOCUSED ELECTRIC FIELDS IN MICROFLUDIC SYSTEMS AND USE THEREOF

(75) Inventors: Owe Orwar, Hovås (SE); Mattias Karlsson, Göteborg (SE); Daniel Chiu, Seattle, WA (US); Anette Stromberg, Västra Frölunda (SE); Anders Karlsson, Bollebygd (SE)

(73) Assignee: Cellectricon AB, Gothenburg (CH)

( * ) Notice: Subject to any disclaimer, the term of this patent is extended or adjusted under 35 U.S.C. 154(b) by 200 days.

(21) Appl. No.: 09/996,559

(22) Filed: Nov. 30, 2001

(65) Prior Publication Data

US 2003/0104588 A1 Jun. 5, 2003

(51) Int. Cl.
*C12N 13/00* (2006.01)
*C12N 15/02* (2006.01)
*C12N 15/87* (2006.01)

(52) U.S. Cl. .................. 435/173.6; 435/450; 435/461

(58) Field of Classification Search ................ 435/450, 435/285.2, 461, 173.6
See application file for complete search history.

(56) References Cited

U.S. PATENT DOCUMENTS

| | | | | |
|---|---|---|---|---|
| 4,959,321 A | * | 9/1990 | Preece et al. | 204/604 |
| 5,100,627 A | * | 3/1992 | Buican et al. | 422/108 |
| 5,945,577 A | * | 8/1999 | Stice et al. | 800/24 |
| 6,020,170 A | * | 2/2000 | Steenbakkers | 435/70.21 |
| 6,221,677 B1 | * | 4/2001 | Wu et al. | 436/518 |
| 6,492,175 B1 | * | 12/2002 | Müller et al. | 435/450 |

FOREIGN PATENT DOCUMENTS

WO WO 200037628 A1 * 6/2000

OTHER PUBLICATIONS

Microfluidic Device for Combinatorial Fusion of Liposomes and Cells, Anette Strömberg, et al., Department of Chemistry, Göteborg University, S-412 96, Göteborg, Sweden, Analytical Chemistry, Reprinted from vol. 73, No. 1, pp. 126-130, Jan. 1, 2001.

* cited by examiner

*Primary Examiner*—Jean C. Witz
*Assistant Examiner*—Susan Hanley
(74) *Attorney, Agent, or Firm*—David G. Conlin; Stephana E. Patton; Edwards & Angell, LLP

(57) ABSTRACT

An apparatus and method are disclosed for electromanipulation of at least one cell or cell-like structure having cell-like membranes, the method comprising the steps: (a) at least one cell or cell-like structure is transported from one or more sample containers located on a chip through microchannel(s) located on said chip into a chamber located on said chip, wherein said chamber contains electrode(s) connected to a voltage generator, wherein said microchannel provides a fluid contact between the sample containers, (b) said cell or cell-like structure(s) is placed close to said at least one electrode, and (c) an electrical field is applied and focused on said cell or cell-like structure(s), said electrical field being of a strength sufficient to obtain pore-formation or fusion of said at least one cell or cell-like structure with another cell or cell-like structure(s) present in said chamber.

69 Claims, 9 Drawing Sheets

METHOD AND APPARATUS FOR MANIPULATION OF CELLS AND CELL-LIKE STRUCTURES FOCUSED ELECTRIC FIELDS IN MICROFLUDIC SYSTEMS AND USE THEREOF

FIELD OF THE INVENTION

The present invention relates to manipulation of cells and cell-like structures using focused electric fields in microfluidic systems. Specifically, the present invention relates to an electrofusion-based method for combinatorial synthesis of at least two individual structures of cellular or subcellular dimensions using microfluidic systems. The present invention also relates to an electroporation-based method for altering the contents of at least one cell or cell-like structure in microfluidic systems.

BACKGROUND OF THE INVENTION

Cell Fusion

The ability to fuse together artificially two types of cells to generate a third cell, which displays hybrid characteristics of the two unfused cells, plays a central role in biotechnology. The development of monoclonal antibodies by Koehler and Milstein [see e.g. Kohler, G. & Milstein, C. 1975, Nature, 256, 495–497] for example, relies on the formation of "hybridomas" created by fusing antibody-producing cells with cancerous cells. The cloning of the sheep Dolly by Wilmut and coworkers [Wilmut, I., Schnieke, A. E., McWhir, J., Kind, A. J., Campbell, K. H. S. 1997, Viable offspring derived from fetal and adult mammalian cells, Nature, 385, 810–813] provides another example where the fusion between two types of cells (an adult cell from the mammary gland with an egg cell) played an essential role.

There are a number of methods for carrying out cell-cell fusion in vitro, including the use of chemicals such as polyethylene glycol (PEG), the use of focused laser beams (laser-induced fusion), and the application of pulsed electric fields (electrofusion). Of these methods, electrofusion has developed into an extremely efficient method for the fusion of mammalian cells, mainly because of its mild conditions, which result in a high number of viable fusion products [see e.g. White, K. L. 1995, Methods in Molecular Biology, 48, 283–293]. The application of an electrical field over phospholipid bilayer membranes induces pore formation when the applied potential reaches or exceeds the membrane breakdown potential. Consequently, electro-permeabilization techniques has been used in a wide variety of biological experiments, like electrofusion for the creation of hybridomas and new cell lines [see e.g. Zimmermann, U., et al., 1985, Adv. Biotechnol. Proc. 4, 79–150; Neil, G. A. et al., 1993. Electrofusion, Methods in Enzymology, 220, 174–196; Glassy, M. 1988, Nature, 333, 579–580], in vitro fertilization [see e.g. Ogura, A. et al., 1995, Reprod. Fertil. Dev., 7, 155–159], cloning experiments [see e.g. Van Stekelenburg-Hamers, A. E. P., et al., 1993, Mol. Reprod. Dev., 36, 307–312], [see e.g. Li, H., et al., 1997, J. Neurosci. Methods, 75, 29–32; Lundqvist, J. A., et al., 1998, Proc. Natl. Acad. Sci. USA, 95, 10356–10360], and electroinsertion for the addition of membrane-associated macromolecules, including proteins [see e.g. Mouneimne, Y., et al., 1989, Electroinsertion of xeno-glycophorin into the red blood cell membrane, Biochem. Biophys. Res. Com. 159, 34–40]. Applications of in vivo electrofusion include the incorporation of gonococcal attachment receptors from human HL60 cells to rabbit corneal epithelial tissue as a viable model of human-specific pathogens [see e.g. Heller, R., et al., 1990, Transfer of human membrane surface components by incorporating human cells into intact animal tissue by cell-tissue electrofusion in vivo, Biochim. Biophys. Acta, 1024, 185–188].

Electric-field-induced fusion is widely employed in biomedical research for a population of cells in suspension. Cells are first brought into contact by dielectrophoresis through the application of a low-amplitude, high-frequency AC field and subsequently a fraction of the cells are fused by a strong and short DC pulse. Although bulk electrofusion of large quantities of cells is useful for creating and selecting new cell lines, it cannot be applied to fuse single cells with high precision. The main drawback of carrying out bulk electrofusion (or PEG-induced fusion) inside a fusion chamber is the inability to manipulate and fuse individual cell pairs selectively based on the biological characteristics of the cells; dielectrophoresis brings together cells and align them into pearl chains inside the fusion chamber based on cell polarization. Practical constraints also limit cell fusion to two cell types at a time inside the fusion chamber. Based on statistics, this random fusion between two cell types of equal concentrations will result in 50% heterokaryon formation (fusion of different cell types) and 50% homokaryon formation (fusion of same cell types). In practice, however, cells of different types often align into pearl chains in segregation because of their differences in size and polarization; provided there are "enough" cells within the fusion chamber, there is usually enough intermixing to ensure heterocytotic fusion. It is, therefore, difficult to carry out cell fusion selectively and controllably among many different cell types using this traditional format. To overcome partially some of the drawbacks of this format, several approaches were developed to achieve cell pair selection prior to fusion, including the use of ligand-receptor recognition, flow cytometry, and laser-based single-cell manipulation. In this invention, we describe a new method based on the use of microfluidic channels for the combinatorial fusion of cells and liposomes.

Electroporation

It has for a long time been recognised that cell membranes can be permeabilised by pulsed electric fields (see e.g. Zimmermann, U. Biochim. Biophys Acta, 694, 227–277 (1982) This technique is called electroporation. The membrane voltage, $V_m$, at different loci on phospholipid bilayer spheres during exposure in a homogenous electric field of duration t, can be calculated from:

$$V_m = 1.5 r_c E \cos \alpha [1 - \exp(-\tau/t)] \quad (1)$$

where E is the electric field strength, $r_c$ is the cell radius, $\alpha$, the angle in relation to the direction of the electric field, and t the capacitive-resistive time constant. Pore-formation will result at spherical coordinates exposed to a maximal potential shift, which is at the poles facing the electrodes (cos $\alpha$=1 for $\alpha$=0; cos $\alpha$=−1 for $\alpha$=π). Generally, electric field strengths on the order of from 1 to 1.5 kV/cm for durations of a few µs to a few ms are sufficient to cause transient permeabilisation in 10-µm-outer diameter spherical cells.

Traditionally, electroporation is made in a batch mode allowing for administration of polar solutes into several millions of cells simultaneously. The electrodes producing such fields can be several square centimetres and the distance between the electrodes several centimetres, thus requiring high-voltage power sources to obtain the needed electrical field strength to cause electrically induced permeabilisation of biological membranes.

Instrumentation that can be used for electroporation of a small number of cells in suspension (K. Kinosita, Jr., & T. Y. Tsong, T. *Biochim. Biophys. Acta*, 554, 479–497(1979); D. C Chang, *J. Biophys.*, 56, 641–652 (1989; P. E. Marszalek, B. Farrel, P. Verdugo, & J. M. Fernandez, *Biophys. J.*, 73, 1160–1168 (1997)) and for a small number of adherent cells grown on a substratum (Q. A. Zheng, & D. C. Chang, *Biochim. Biophys. Acta*, 1088, 104–110 (1991); M. N. Teruel, & T. Meyer *Biophys. J.*, 73, 1785–1796 (1997)) have also been described. The design of the electroporation device constructed by Marszalek et al. is based on 6 mm long 80 μm diameter platinum wires that are glued in a parallel arrangement at a fixed distance of 100 μm to a single glass micropipette. The design by Kinosita and Tsong uses fixed brass electrodes spaced with a gap distance of 2 mm, the microporator design of Teruel and Meyer relies on two platinum electrodes that are spaced with a gap distance of about 5 mm, and the electroporation chamber design by Chang uses approximately 1 mm-long platinum wires spaced at a distance of 0.4 mm. It is obvious, that these electroporation devices create electric fields that are several orders of magnitude larger than the size of a single cell which typically is 10 μm in diameter, and thus can not be used for exclusive electroporation of a single cell. They are also not optimal for use in a micofluidic device.

Microfluidics

Microfluidic systems provide an attractive and versatile platform for the manipulation, isolation, and transport of selected cells prior to either electric-field induced manipulation of cells or by manipulation of cells by other means, such as chemical-induced, or laser-induced fusion of cells. Microfabricated networks of micron-sized channels have already proven useful for applications in chemical separations (e.g. capillary electrophroesis), biochemical assays, DNA analyses, medical diagnostics, drug delivery, and cell manipulation and sorting. The ease with which arrays of microelectrodes can be patterned and integrated with networks of microchannels makes microfluidic systems an especially attractive platform for applications in electrofusion in which fusion among a multitude of different cell types is desired.

It is time consuming and impractical to use bulk fusion and electroporation chambers for applications involving a large number of cell types and fusion or electroporation events. With chip-based microfluidic systems, however, a large number of cells can be transported, combined, separated, and sorted; cell fusions and electroporations can be achieved on-chip either in parallel or in rapid sequence. In addition, the amount of cells required for each cell type may be dramatically reduced owing to the reduced volumes in the microchannels (in comparison with fusion or elcetroporation chambers) provided the cell fusion or electroporation and survival yields are acceptable.

Liposomes

Liposomes are synthetic lipid-bilayer containers that can be used to mimic the surface properties of natural biological compartments. The sizes of these containers can also be varied from tens of nanometers to tens of micrometers in diameter (which correspond to $10^{-21}$ to $10^{-12}$ L) for mimicking the natural size distribution of organellar and cellular compartments. These versatilities together with the ease that protein functions can be reconstituted in liposomes make them attractive as reaction containers for approximating the in vivo conditions where biochemical reactions occur [see e.g. Chakrabarti, A. C.; Breaker, R. R.; Joyce, G. F.; Deamer, D. W. J. Mol. Evol. 1994, 39, 555–559; Oberholzer, T.; Albrizio, M.; Luisi, P. L. Chem. Biol. 1995, 2(10), 677–682; Oberholzer, T.; Wick, R.; Luisi, P. L.; Biebricher, C. K. Biochem. Biophys. Res. Commun. 1995, 207(1), 250–257; Steinberg-Yfrach, G.; Rigaud, J. L.; Durantini, E. N.; Moore, A. L.; Gust, D.; Moore, T. A. Nature, 1998, 392 (6675), 479–482; Oberholzer, T.; Meyer, E.; Amato, I.; Lustig, A.; Monnard, P. A. Biochim. Biophys. Acta 1999, 1416, 57–68]. Reactions in these systems have been measured, typically, as an ensemble average from millions of liposomes and may therefore hide interesting information concerning reaction rates and mechanisms. Recently, methods have been developed where chemical reactions can be initiated in single liposomes using microinjection [see e.g. Bucher, P.; Fischer, A.; Luisi, P. L.; Oberholzer, T.; Walde, P. Langmuir 1998, 14(10), 2712–2721], electroinjection, electroporation [see e.g. Miyata, H.; Nishiyama, S.; Akashi, K.; Kinosita, K. Proc. Natl. Acad. Sci. U.S.A. 1999, 96(5), 2048–2053; Chiu, D. T.; Wilson, C. F.; Ryttsén, F.; Strömberg, A.; Farre, C.; Karlsson, A.; Nordholm, S.; Gaggar, A.; Modi, B. P.; Moscho, A.; Garza-López, R. A.; Orwar, O.; Zare, R. N. Science 1999, 283, 1892–1895], and electrofusion [see e.g. Chiu, D. T.; Wilson, C. F.; Ryttsén, F.; Strömberg, A.; Farre, C.; Karlsson, A.; Nordholm, S.; Gaggar, A.; Modi, B. P.; Moscho, A.; Garza-López, R. A.; Orwar, O.; Zare, R. N. Science 1999, 283, 1892–1895]. In combination with single-molecule detection techniques [see e.g. Nie, S., Zare, R. N., Annu. Rev. Biophys. Biomol. Struct., 1997, 26, 567], these single-liposome manipulation methodologies provide a powerful set of tools for studying chemical reactions inside liposomes at a level of detail that was previously unattainable [see e.g. Chiu, D. T.; Wilson, C. F.; Ryttsén, F.; Strömberg, A.; Farre, C.; Karlsson, A.; Nordholm, S.; Gaggar, A.; Modi, B. P.; Moscho, A.; Garza-López, R. A.; Orwar, O.; Zare, R. N. Science 1999, 283, 1892–1895; Chiu, D. T.; Wilson, C. F.; Karlsson, A.; Danielsson, A.; Lundqvist, A.; Strömberg, A.; Ryttsén, F.; Davidson, M.; Nordholm, S.; Orwar, O.; Zare, R. N. J. Chem. Phys. 1999, 247, 133–139].

In order to understand chemical behaviors relating both to intrinsic properties of the reaction system as well as to properties of the reaction surroundings, and to be able to optimize conditions for a given liposome-confined reaction, design and knowledge of the liposome reactor is of central importance. Container size, topography, surface charge, wetability as well as the phospholipid and membrane protein composition of a liposome reactor are some important properties that needs to be controlled. A seemingly simple issue such as variations in compartment size might have profound effects on both reactivity and mechanisms for a given enzyme-catalyzed reaction [see e.g. Chiu, D. T.; Wilson, C. F.; Karlsson, A.; Danielsson, A.; Lundqvist, A.; Strömberg, A.; Ryttsén, F.; Davidson, M.; Nordholm, S.; Orwar, O.; Zare, R. N. J. Chem. Phys. 1999, 247, 133–139; Mikhailov, A., Hess, B., J. Phys. Chem. 1996, 100, 19059–19065].

SUMMARY OF THE INVENTION

In order to better understand the nature of individual cells and their interactions with the extracellular environment, it is often desirable to selectively and controllably perturb single cells and to study the cellular reactions to this perturbation. To address this challenge and to overcome the shortcomings of bulk electrofusion and bulk electroporation, the inventors of the present invention have developed a technique to electroporate at least on cell or fuse together at least two cells or cell-like structures at a time. The ability to controllably fuse or electroporate together small numbers of cells represents a technique by which the long term genetic identity and behavior of a selected cell can be precisely manipulated, and opens up new possibilities to create, for example, combinatorial libraries of hybrid cells. The ability to fuse many different cell types together is important in applications in which a combinatorial library of fused cells is required. Today, there is noare few techniques for the combinatorial fusion of multiple cell types. For the generation of such libraries, the inventors have developed a chip-based method to store, select, transport, and fuse or electroporate cells or cell-like structures.

According to the present invention cells or cell-like structures are placed in different storage containers on a microchip structure. The microchip can be fabricated in a variety of materials, including but not limited to plastic, polymer, silicon, silicone, glass etc. using known microfabrication methods. Said cells or cell-like structures of different type are placed in different said storage containers in such a way that a given container contains only one cell type, said cell type being a known cell type. Sometimes it is preferable that the storage containers contain several cell types. Cells are transported from different storage containers on demand, through microchannels, to a fusion or electroporation chamber on the chip using, for example, optical trapping and device translation. Other types of cell transportation are also possible such as; optical trapping of beads tethered to cells, electrophoretic, electroendoosmotic, dielectrophoretic and through pressurized liquid flows. In the fusion or electroporation chamber, e.g. hybrid cells are formed by using microelectrode-assisted electrofusion or gene-fragments are introduced to a cell using micro-electrode-assisted electroporation. In cases where electroporation is used, the agents to be internalized can be supplemented locally to the electroporation chamber through microchannels. Following electrofusion or electroporation cells may be transported to storage containers on the chip for treated or manipulated cells. The cells may even be cultured on the chip prior to and following electromanipulation.

This chip-based technique is useful generally in situations where multiple cell types are involved, because in single cell-cell electrofusions one of the main difficulties is to identify with light microscopy the different cell types to be fused. By using different storage chambers from which an identified cell type can be selected, total control of the identity of the fusion partners can be achieved. These electromanipulation techniques, in combination with a powerful measurement and imaging technique, can control precisely the genetic and biochemical nature of single cells.

Alteration of cellular properties can also be achieved by fusing together a synthetic lipid vesicle with the desired vesicular content and membrane compositions to a target cell. This technique can be used to alter the molecular contents and membrane properties of single cells. It is, for example, possible to introduce a membrane protein reconstituted in liposomes into the cell plasma membrane. This ability to selectively transform the membrane composition of single cells is anticipated to have useful biological applications, such as the introduction of surface receptors for the screening of potential ligands and related pharmacological compounds.

Thus, the present invention provides a novel method for the selective electrofusion and electroporation of cellular structures, such as cells and liposomes. This method offers the advantage of cell-selection, fusion of adherent cell structures with a high spatial resolution, giving the possibility to create complex cellular networks. As electrofusion is a mild method, this miniaturized version can e.g. be used for cloning on the single cell level and for in vitro fertilization. For cloning experiments in particular, the shortcomings of bulk electrofusionporation is overcome with the present technique as it offers complete control over the fusion process and any doubts to the identity of the somatic cells needs not to be raised. Also most importantly, this method, preferentially in combination with micromachined chip technology, can be used to create screening libraries of cloned cells or hybrid cells.

The present invention also relates to a method whereby the interior contents of at least one liposome or at least one cell can be altered on demand using electroporation. Electrofusion and electroporation can be carried out using the same instrumental setup. Liposomes as well as many cell types are indistinguishable on the light-microscopic level, making sorting and handling difficult. The present invention provides a microchannel device that in combination with optical trapping, and an electrofusion or electroporation system enables this. This technique also offers means to initiate multi-component reactions. In addition to having the ability to tailor reaction environments for studies of biochemical reaction dynamics, combinatorial liposome fusion can be implemented for ultra-small-scale chemical derivatization in microchemical separations and micro total-analysis-systems.

Electrofusion of single pairs of cells that were identified based on their different size have previously demonstrated [Strömberg, A. et al., Proc. Natl. Acad. Sci. U.S.A. 2000, 97, 7–11]. According to the present invention, this concept is extended to fusion of cells that are morphologically identical on the light-microscopic level. This enables the controlled combination of any two cells with similar appearance but, for example, different genetic composition. Therefore, the technique according to the invention is useful in the production of cell hybridomas [see e.g. Zimmermann, U.; Vienken, J.; Halfmann, J.; Emeis, C. C. Adv. Biotechnol. Processes 1985, 4, 79–15], cloning [see e.g. Willmut, I.; Schnieke, A. E.; McWhir, J.; Kind, A. J.; Campbell K. H. S. Nature, 1997, 385, 810–813] and studies of genetic expression [see e.g. Kucherlapti, R. S., Ruddle, F. H.; Ann. Intern. Med. 1975, 83, 553–560].

The characterizing features of the invention will be evident from the following description and the appended claims.

BRIEF DESCRIPTION OF THE DRAWINGS

In the description and the example below, reference is made to the accompanying drawings. The drawings comprise the following figures:

FIG. 1B is a photomicrograph that shows a microchannel at the interfacial region between a cell storage container and the reaction chamber. Scale bar represents 70 µm. FIG. 1C shows a trapped cell inside a 30 µm i.d. capillary during transport. Scale bar represents 15 µm. FIG. 1D shows bright-field, and FIG. 1D shows fluorescence images of a fluorescein-containing (10 µM) liposome after transfer from its storage depot to the fusion chamber. The background fluorescence from the surrounding solution was decreased more than 100-fold. Scale bar represents 10 µm.

Figure 5:
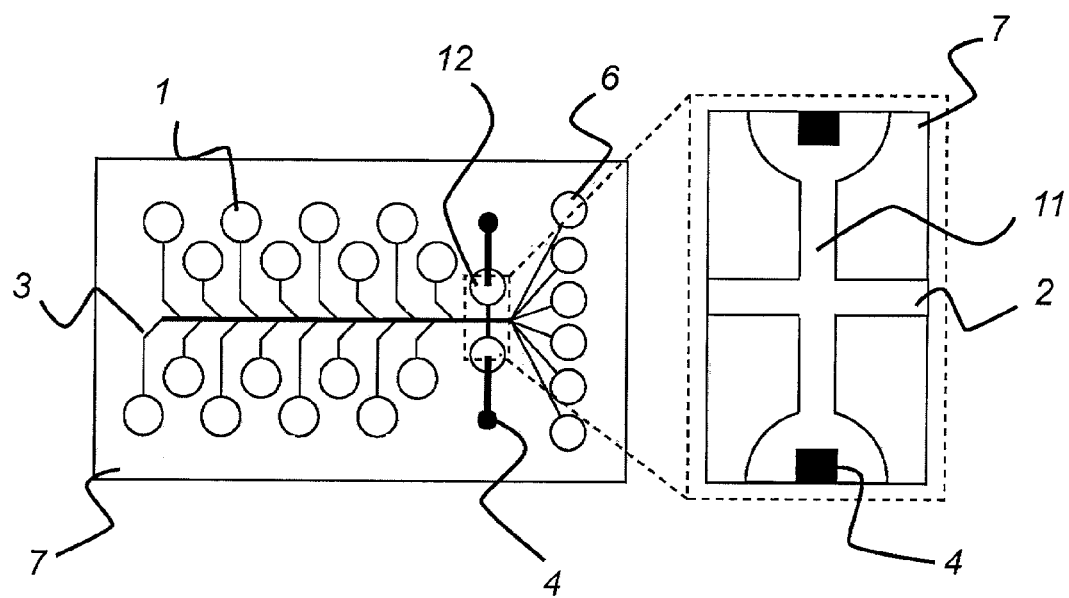

A chip-structure suitable for both electroporation and combinatorial fusion is illustrated in FIG. 5. This structure uses on-chip electrodes placed at a distance from the cells under treatment and the current required for electroporation in carried by the electrolyte contained in the microchannel in the electrofusion electroporation chamber.

Figure 6:
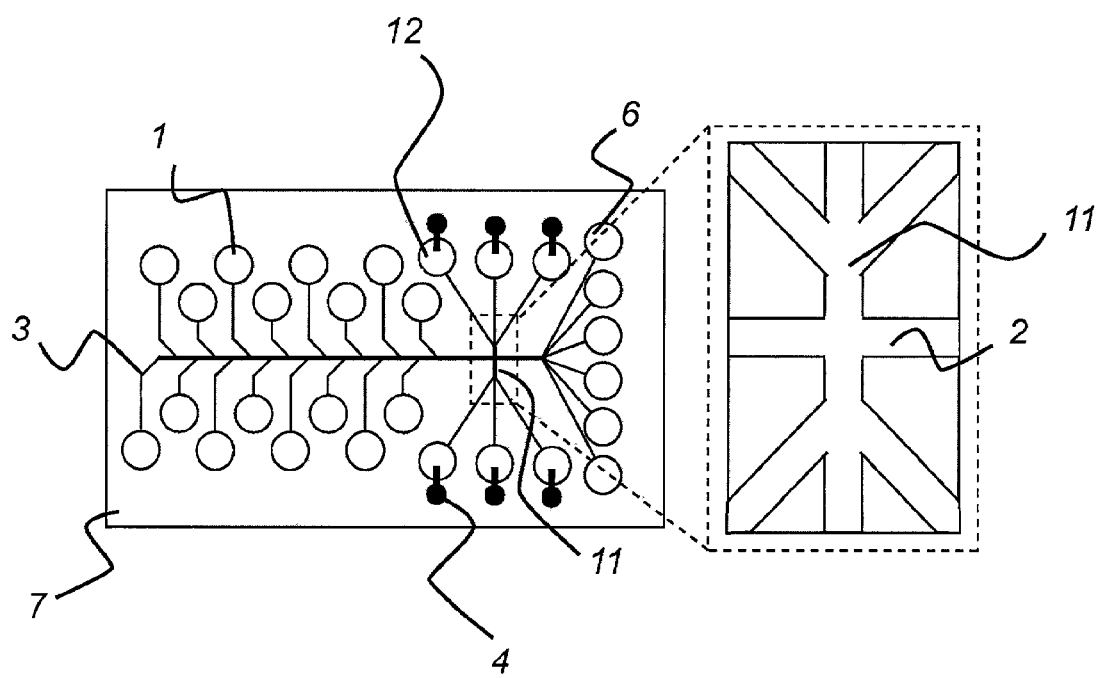

Another microfluidic chip for combinatorial electrofusion and electroporation is illustrated in FIG. 6. This chip is equipped with several electrodes connected to several electrolyte channels.

Figure 7:
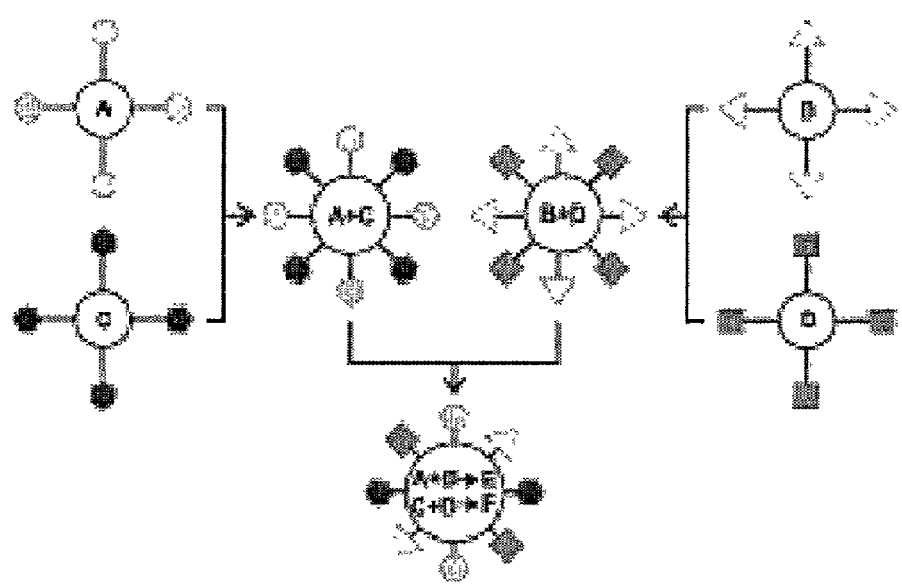

FIG. 7. Schematic of pair-wise fusion of liposomes to create hybrid liposomes. Boxes, hexagons, circles and triangles represent different phospholipids, membrane proteins, or other membrane specializations, and A,B,C,D represents different reactants. Individual liposomes are sequentially fused as shown in the figure, thereby creating new types of liposomes. In the figure, the liposome denoted A is fused with liposome C. This fusion is followed by the fusion of liposome B and D. The final fusion involves the fusion of these new types of liposomes, thereby mixing both membrane composition and aqueous interior from all four starting liposomes in the final product liposome. As a result of this fusion, two parallel reactions are initiated (A+B→E and C+D→F) in a well-defined nanoenvironment. From four different starting liposomes, 11 different product liposomes can be created.

Figure 8:
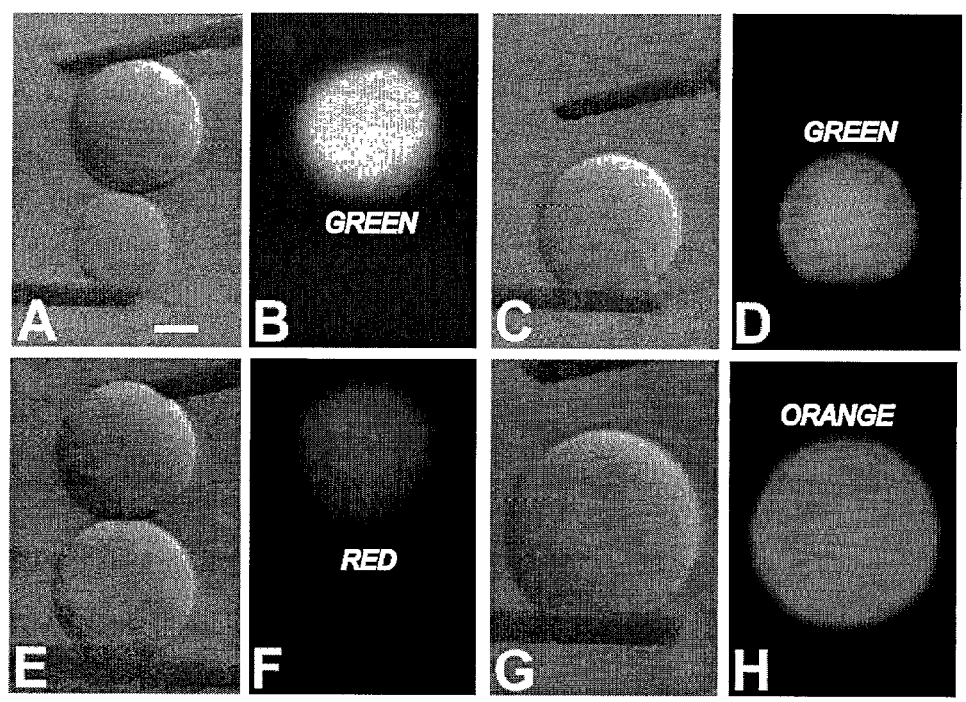

FIG. 8. Sequential pair-wise fusion of three different liposomes. The first fusion involves a "plain" liposome (no membrane dye in the membrane) and a liposome with the membrane fluorescent dye DiO (A-C). The membrane dye distributes evenly over the entire membrane surface in the product liposome (D). In the next fusion the created "hybrid" liposome with DiO was fused with a liposome with the membrane fluorescent dye DiI (E-G). DiI was distributed over the entire membrane surface of the product "hybrid" liposome (H). B/W fluorescence images were pseudocolor-coded and enhanced digitally. Scale bar is 10 µm.

Figure 9:
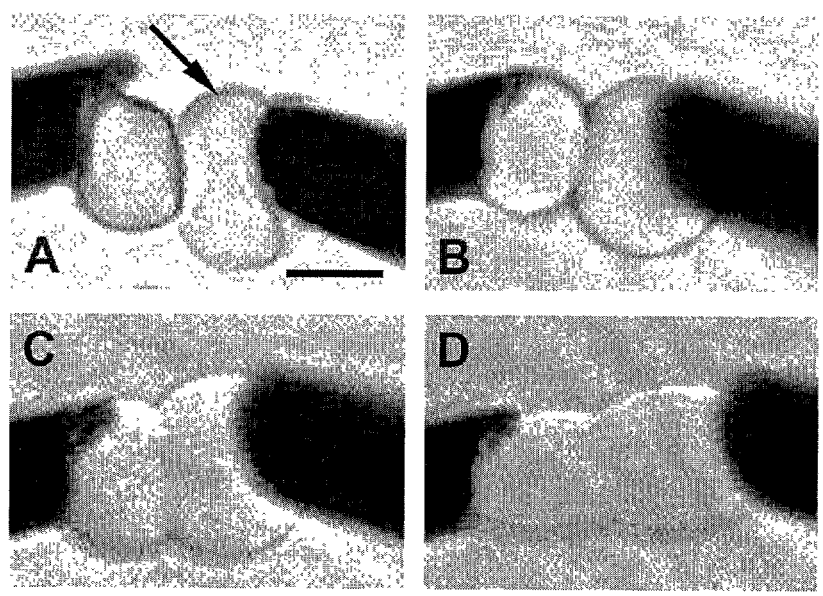

FIG. 9. Selective single cell-cell electrofusion. In this case a transported Red Blood Cell (RBC) (indicated with an arrow) is fused to a stationary, non-transported RBC. (A) The electrodes are used to place the RBCs in close contact to each other. As this close contact can be achieved mechanically, dielectrophoresis is not necessary. (B) Fusion is in progress and the contact zone between the cells is no longer distinct. Due to electroporation in the slightly hypo-osmolar fusion medium, the cells are somewhat tumid. (C) Fusion is completed. The greyish line that seems to divide the fused cell into two halves, is the waist of the dumbbell shape of the fused cell. As the cytoskeleton is intact inside the RBCs, total rounding up of the fused cell is not achieved. (D) A gentle pulling force was applied by the microelectrodes, to show that the cells were fused. Scale bar is 5 µm.

DETAILED DESCRIPTION OF THE INVENTION

A method for electromanipulation of at least one cell or cell-like structure having cell-like membranes, comprising the following consecutive steps:

(a) at least one cell or cell-like structure is transported from one or more sample containers located on a chip through at least one microchannel located on said chip into a chamber located on said chip, wherein said chamber contains at least one electrode connected to a voltage generator, and wherein said microchannel provides a fluid contact between the sample containers, (b) either said at least one cell or cell-like structure is placed or aligned close to said at least one electrode, or said at least one electrode is placed or aligned close to said at least one cell or cell-like structure in said chamber, (c) an electrical field is applied and focused on said at least one cell or cell-like structures, said electrical field being of a strength sufficient to obtain pore-formation in said at least one cell or cell-like structure or sufficient to obtain fusion of said at least one cell or cell-like structure with another cell or cell-like structures present in said chamber.

An important feature is that the transportation of the fusion partners in step (a) does not take place spontaneously. This means that this transportation is always actively controlled according to the invention.

An apparatus for electromanipulation of at least one cell or cell-like structure having cell-like membranes, said apparatus comprising one or more sample containers for said cell or cell-like structure in fluid contact through at least one microchannel with a fusion chamber, optical trapping means for transport of individual cells or cell-like structures through said at least one microchannel into the fusion chamber, and at least one microelectrode connected to a voltage generator for providing a focused electrical field in the fusion chamber, wherein said sample container, said microchannel and said fusion chamber are placed on a chip.

Furthermore, the invention relates to the use of the above method and the above apparatus.

Said at least one cell or cell-like structure having cell-like membranes (below sometimes also called fusion partners) are preferably structures of cellular or subcellular dimensions. The expression "structure of cellular or subcellular dimensions" relates in particular to biological structures such as independent cells and smaller structures, but it also relates to similar artificial structures. Thus, the fusion partners as well as electroporated cells and cell-like structures may be, independently of each other, a single cell, a liposome, a proteoliposome, a synthetic vesicle, a plant protoplast, an egg cell, a sperm or spermatid, and an enucleated egg cell.

For fusion, the cells or cell-like structures constituting the fusion partners are brought into contact with each other. This means either that they are placed so that the outer surfaces of the fusion partners are touching, or that the fusion partners are placed at a very small distance from each other.

According to the invention it is thus possible to fuse many similar or different fusion partners, e.g. in order to create multinuclear cells with more than two nuclei, or in order to introduce a substance contained in vesicles into a cell. It is possible to repeat the steps of the method according to the invention one or several times, so that a new fusion partner is fused to two already fused fusion partners, which is of particular importance when combinatorial libraries of cloned cells and hybrid cells are created. When, e.g. the two fusion partners are liposomes, the fusion of them allows both the introduction of the content of one liposome into the interior of the other liposome. It is also possible and to add lipids and membrane proteins from the liposome membrane oninto the cell surface. This cell-liposome fusion represents a novel approach to the manipulation of the membrane contents and surface properties of single cells.

To fuse the two fusion partners it is necessary to place them next to each other, i.e. in contact with each other. The fact that the two fusion partners are placed next to each other before fusion makes it possible to avoid dielectrophoresis, which traditionally is used for the creation of close contact between cells. However, dielectrophoresis can be used successfully in combination with this invention to create and establish close cell-cell contacts before the dc-field fusion pulse is applied. Mechanically, close contact between the fusion partners can be done in any suitable way. Individual manipulation of the two fusion partners for alignment facilitates this alignment. The fusion partners may be manipulated by the microelectrodes provided in step (c).

When electrodes are used for positioning of the fusion partners, it is possible to align the two fusion partners by adjusting their positions by moving them with the tips of the electrodes. In order to move the electrodes it may be advantageous to use a microscope, at least one micropositioner and/or a stereotactic device. In some cases it may be advantageous to use dielectrophoresis, as pretreatment of the two aligned cells, before fusion. This can be done by connecting an ac-field function generator to the electrodes.

The electrical field may be obtained by use of a low-voltage or high-voltage pulse-generator depending on the electrodes used, and other experimental parameters. The voltage generator is used to produce an electric field strength sufficient to result in fusion between the two fusion partners, as well as pore formation in one cell structure and is approximately 0.1–10 kV/cm, for durations of 10 μs to several seconds. The voltage measured at the membrane of the fusion partners and electroporated cells should be between 10 mV to several volts, preferably around 0.5 V. In the case of multiple-voltage-pulse protocols, the inventors have found that a pulse repetition rate of approximately 1 Hz, to be suitable. However, other repetition rates might work well. For longer pulse-application durations, correspondingly, repetition rates of a lower frequency should be used. In any event, the length and the strength of the pulses depend on the size of the partners to be fused. Preferably, the applied voltage pulses have a rectangular waveform, but other waveforms works as well, including various ac-field pulse protocols. For dielectrophoresis, the sweep function generator preferably generates an alternating field, sineu-wave form, of field strengths between 100 V/cm–5 kV/cm, 100 Hz–2 MHz.

The electrical field used to obtain fusion or electroporation should be highly focused in order to avoid affecting any surrounding structures and to obtain the advantages of the present invention. To focus the electrical field it is preferable to provide the electrical field by use of one or two microelectrodes positioned close to the two fusion partners, i.e. 0–10 μm, preferably 0–5 μm, from the cellular membrane. In the case of using a single electrode, this electrode is preferably, biased at a positive potential (anode) and work against a grounded cell preparation.

According to the invention the microelectrodes are preferably electrodes of cellular to subcellular dimensions. Preferably the outer dimension of the ends of the electrodes positioned closest to the fusion partners is from a few nanometers to ~100 micrometers, more preferably 1–30 micrometers and most preferably approximately 10 μm. The electrodes can be made of a solid electrically conducting material, or they can be hollow for delivery of different chemical agents into the fusion container. The electrodes can be made from different materials. A special type of electrodes are hollow and made from fused silica capillaries of a type that frequently is used for capillary electrophoresis and gas chromatographic separations. These capillaries are typically one to one hundred micrometers in inner diameter, and five-to-four hundred micrometers in outer diameter, with lengths between a few millimeters up to one meter. For cell fusion applications, these electrodes are filled with an electrolyte, preferably a physiological buffer solution. When a potential sufficient to cause cell-fusion is applied over the capillary, electroendoosmotic bulk flow is induced in the capillary, which in combination with Poiseuille flow (gravitational flow in capillaries) can be used to efficiently transfer materials to the fusion partners. Such hollow narrow-bore fused silica capillaries have the additional advantage that components added to the inlet end can be fractionated based on their charge-to-frictional drag ratio. This characteristic feature of the system can be used to, for example, investigate the effect of various fractionated components on cell fusion and cell electroporation.

The electrodes used in the present invention are preferably of a movable type that can be positioned at will close to a cell or a cell-like structure. Preferably such electrodes are controlled by micromanipulators. The electrodes can also be fabricated directly on chip. Such electrodes can be movable in a microelectromechanical device but they can also be stationary. Electrodes can be fabricated on-chip in a variety of materials. For example, metal electrodes can be deposited on silicon using evaporation or sputtering. Furthermore, it is preferred to provide the fusion partners in an electrofusion buffer in the sample containers.

The fusion partners may also be exposed to a dielectrophoretic field in a buffer prior to step (b), and they may also be treated with a fusogenic or other agent that promotes close cell-cell contacts prior to step (b). Furthermore, it may also be advantageous to pre-electroporate at least one of the fusion partners prior to step (b).

For electrofusion and electroporation involving multiple cell types, a chip-based technique is disclosed for selecting, transporting, purifying, fusing or electroporating, and storing treated cells. A chip may be constructed with sample containers for cells of different types. The sample containers haves fluid contact with the fusion or electroporation container through microchannels. Optical trapping is used to transport individual liposomes and cells through the microchannels into the fusion container. Other types of cell transportation are also possible such as; optical trapping of beads tethered to cells, electrophoretic, electroendoosmotic, dielectrophoretic and through pressurized liquid flows. In the fusion container, selected pairs of cells are fused together or electroporated using micromanipulator-controlled microelectrodes or stationary electrodes. In addition to the fact that different fusion partners can be easily identified and selected using such chip-based structures, cells can be kept in the storage chambers containing physiological buffers or growth media until they are to be fused in another type of suspension media, for example, a low conductive—low osmolarity buffer in the fusion chamber; fused cells also can be moved rapidly to a chamber with postfusion medium for recovery.

Figure 2:
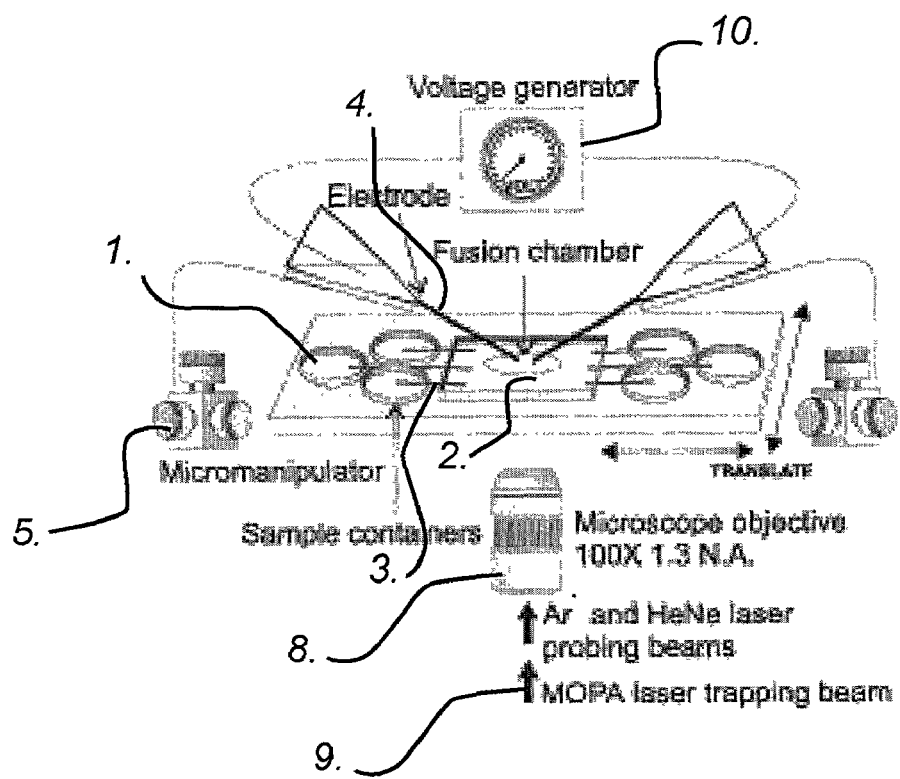
FIG. 2. Schematic picture of a microfluidic device, consisting of sample containers 1, microchannels 3, and a fusion/electroporation chamber 2. The chip is placed on the stage of an inverted microscope coupled to the microelectrode system. The microelectrodes 4, were connected to a voltage generator and were positioned using micromanipulators 5. The outputs from $Ar^+$ (488 nm) and HeNe (633 nm) lasers were used for excitation of dyes and a MOPA laser (993 nm) was used for optical trapping. All the laser beams were sent through a 100× oil immersion microscope objective of high numerical aperture (1.3 N.A.).

An apparatus according to the invention or a setup suitable for performing the method according to the invention is illustrated in FIG. 2. Cells or cell-like structures are provided in sample containers 1. They are then transported, preferably, one at a time through microchannels 3 into a fusion container 2. The sample containers and the fusion container may be placed on a microscope coverslip mounted in a polycarbonate holder above a microscope objective 8 (e.g. 100×1.3 N.A.).

The fusion partners may be prealigned using optical trapping (such as a MOPA laser trapping beam 9, or simply by pushing them together with the microelectrodes 4, (in the setup according to FIG. 2, two electrodes are used) controlled by high-graduation micromanipulators 5. The microelectrodes are preferably carbon fiber electrodes, and most preferably carbon fiber ultramicroelectrodes (5 μm in diameter).

A voltage generator 10 is used to provide the required electrical field.

Figure 3:
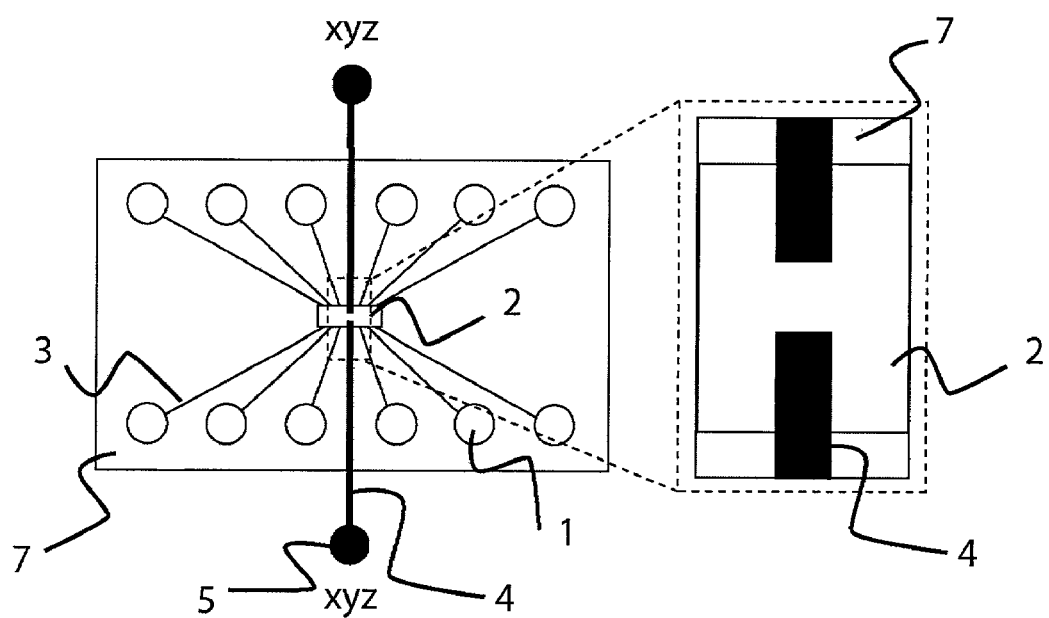
In FIG. 3, a microfluidic chip for microelectrofusion/microelectroporation is illustrated. In this configuration, external microelectrodes controlled by micropositioners are used for manipulation of the cells in the electrofusion/electroporation chamber.

FIG. 3, shows a chip 7, for microelectrofusion and microelectroporation using external electrodes 4, controlled by micromanipulators 5. In this structure, several sample containers 1, are connected via microchannels 3, to an elecrofusion/electroporation chamber 2, where cell-manipulation takes place. In this configuration, external microelectrodes controlled by micropositioners are used for manipulation of the cells in the electrofusion/electroporation chamber.

Figure 4:
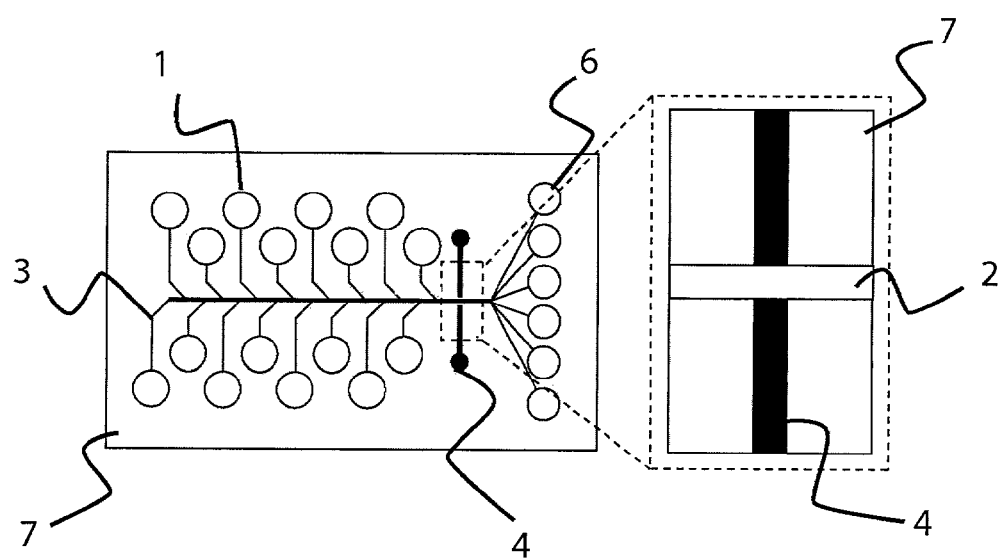
In FIG. 4, a fully integrated chip-structure for combinatorial electrofusion/electroporation with storage containers for treated/manipulated cells is illustrated. In this configuration the electrodes are integrated on-chip.

In FIG. 4a fully integrated chip-structure 7, for combinatorial electrofusion and electroporation is illustrated. This structure is comprised of several sample containers 1, for untreated cells, an electrofusion/electroporation container 2, and several storage containers 6, for manipulated cells. Cells are transported in microchannels 3. In this configuration the electrodes used for electrofusion are integrated on-chip. However, they may be external and operated by micropositioners as in FIG. 3.

Another example of a chip-structure 7, suitable for both electroporation and combinatorial fusion is illustrated in FIG. 5. This chip is similar to the chip illustrated in FIG. 4, the main differences it that the current needed for elecrofusion or electroporation is provided via an electrolyte-filled channel 11, integrated on the chip rather than directly from the microelectrodes 4. When using this structure for electroporation, the cell-loading agent to be introduced into the cell is supplemented to the electrolyte filled channel via inlet wells 12. This chip is also equipped with storage containers 6, for treated cells, and microchannels 3, for transport of cells.

Yet another example of chip structure for both combinatorial electrofusion and combinatorial electroporation is illustrated in FIG. 6. In this configuration the chip structure 7, is composed of sample containers for untreated cells 1, an electrofusion/electroporation chamber 2, and storage compartments for manipulated cells 6. The chip also contains microhannels 3, for transport of cells. The electrofusion/electroporation station is composed of an electrolyte-filled microchannel connected to several wells 12, each containing one type of cell-loading agents. In addition each well is equipped with individually addressable electrodes 4.

The method and the apparatus according to the invention are suitable for manipulating the genetic identity and biochemical surface properties of individual cellular or subcellular structures, such as organelles. It is especially suitable and interesting for in vitro-fertilization. It can also be used in several other applications such as cloning, creation of hybridomas, manipulation of the composition of a cellular membrane, and delivery of a well-defined volume of a substance to a cell (particularly delivery of a pharmaceutically active substance to a cell). The method and apparatus according to the invention is suitable for creating combinatorial libraries of hybrid cells, preferentially in combination with micromachined chip technologies.

To date, very few methods allow detailed design of complex biochemical reaction systems that offer the experimenter control of both local activities and the nanoenvironment of an enclosed reaction system. The presented technology is one step toward that goal where such nanoenvironments can be provided by liposomes by their variability in size, membrane wall properties such as charge (e.g. lipid composition and protein content) and the composition of the aqueous interior (e.g. ionic strength and reactants). For complex reaction systems involving, for example, multiple reactants such as enzymes and substrates, the exact order of reaction can be specified and defined by the fusion sequence. The complex liposomes can be characterized with a wide range of spectroscopic and electrochemical techniques to elucidate their catalytic activity, ion permeability, and other properties as a function of biocompartment composition and size. This liposome selection and fusion technique should also be useful for ultra-small scale chemical derivatizations, in combination with microseparations.

The usage of optical trapping for the handling of cells requires that trapping leaves the cells undamaged. There are indications which show that trapping parameters can be optimized so that cells are kept viable and reproductive [Liang, H., Vu, K. T., Krishnan, P., Trang, T. C., Shin, D., Kimel, S., Berns, M. W., Biophys. J., 1996, 70, 1529–1533]. The RBC-fusions presented here is a logical extension of our previous single cell-cell electrofusions. The invention can also be used in performing cell-liposome electrofusions.

Importantly, Tthe cell-selection/fusion concept using microfluidic systems according to the invention can be advantageously used for the production of hybridomas and, cloning, and cell-liposome fusions. In addition to electrofusion, such microfluidic systems are complementary to chemical-induced (e.g. PEG) fusion, or as a platform for integrating chemical-induced fusion and electrofusion. The presence of a small amount of PEG, for example, can increase the success of electrofusion. It is also well known that a number of chemical and biological factors affect the yield of fusion. The osmolality of the medium is one example; fusion yields, for both electrofusion and PEG-induced fusion, increases greatly if carried out in hypotonic media or if cells were treated briefly in hypotonic media then returned to isotonic media for fusion. With microfluidics, varying the osmolality or the concentration of the fusion media inside the channels can be conveniently performed.

The presence of divalent cations (e.g. calcium) and pretreatment of cells with protease are other examples in which fusion yield can be improved dramatically. These chemical and biological conditions, however, vary widely between cells types and the best conditions for carrying out fusion need to be found empirically. In the bulk fusion format, varying these parameters is tedious, whereas microfluidics provides a natural platform for rapidly testing the suitability of each of these conditions.

In addition, this microfluidic format provides the advantage of integration with chip-based microfabricated electrode systems. Such integrated microfluidic-microelectrode system will find use not only for electrofusion, and electroporation but for any electric-field based manipulation of cells. For applications in electroporation, the network of microchannels and containers may each contain a different gene fragment or pharmaceutically active compound, which can be delivered and electroporated into the cells of interest via microchannels and integrated (or external) microelectrode systems. Furthermore, the electrofused or electroporated cells can be cultured on-chip inside such microfluidic systems for further on-chip operations or long-term studies. Such microfluidic systems may be integrated with on-chip fabricated electrodes, or can be interfaced with external electrode systems. Such systems can also be fabricated from a number of substrate materials, including glass, silicon, teflon, or any number of other suitable plastics, such as polyethylene, polymethyl methacrylate, and polydimethylsiloxane. The capabilities offered by such versatile cell manipulation systems will find a wide range of applications, including cell transfection, stem cell research, hybridoma production, monoclonal antibody production, and biosensors, etc.

The invention will now be further explained in the following examples. These examples are only intended to illustrate the invention and should in no way be considered to limit the scope of the invention.

EXAMPLES

Experimental Section

Construction of Microfluidic Device

Microchannels with 10–30 μm i.d. and 30–100 μm o.d. were created by pulling heated borosilicate glass capillaries (0.86 mm i.d. and 1.5 mm o.d. from Clark Electromedical Instruments, Pangbourne, Reading, UK), and cut into smaller pieces, typically 3-to-5 mm long. The capillaries were contacted onto no. 1 borosilicate microscope cover slips using transparent glue (Karlssons, Cederroth, Upplands Väsby, Sweden) by gently pouring the glue in a thin line (about 2 mm thick) over a capillary. The glue was also used to create the barriers between the different containers.

Microscopy and Optical Trapping

Optical trapping and fluorescence imaging systems were built in-house [Chiu, D. T.; Wilson, C. F.; Ryttsén, F.; Strömberg, A.; Farre, C.; Karlsson, A.; Nordholm, S.; Gaggar, A.; Modi, B. P.; Moscho, A.; Garza-López, R. A.; Orwar, O.; Zare, R. N. Science 1999, 283, 1892–1895]. The optical trap was formed by bringing the 992 nm output from a single-mode MOPA laser diode (Model SDL-5762-A6, SDL, Inc., San Jose, Calif., USA) to a diffraction-limited focus with a high-numerical aperture objective (100× oil immersion, N.A. 1.3 Leica, Wetzlar, Germany). The fluorescence excitation was achieved by using the 488-nm output of an argon ion laser (2025-05, Spectra Physics Lasers Inc, Mountain View, Calif., USA) or 633 nm output from a HeNe laser (1145p, JDS Uniphase, Manteca, Calif., USA).

Fluorescence and brightfield images were obtained by a 3-chip color CCD camera (Hamamatsu, Kista, Sweden) and then recorded by a Super VHS recorder. The CCD images were digitized from tape and processed using Argus 20 (Hamamatsu, Kista, Sweden) image-editing package and Adobe Photoshop software.

Liposome Electrofusion

Liposomes were fused using a pair of 5 μm-diameter solid carbon fiber microelectrodes (Dagan Corp, Minneapolis, Minn., USA). The two microelectrodes were positioned by high-graduation micromanipulators (Narishige MWH-3, Tokyo, Japan), and were occasionally used for alignment of liposomes on the substrate before fusion [Chiu, D. T.; Wilson, C. F.; Ryttsén, F.; Strömberg, A.; Farre, C.; Karlsson, A.; Nordholm, S.; Gaggar, A.; Modi, B. P.; Moscho, A.; Garza-López, R. A.; Orwar, O.; Zare, R. N. Science 1999, 283, 1892–1895]. The two electrode tips (anode and cathode) were positioned at an angle of 0–20°, and 160–180° with respect to the object plane, close to the membrane of each fusion partner. Electrofusion of liposomes at room temperature (20° C.) was achieved by applying several (typically 4 to 10) 20–40 μs long pulses using a low-voltage pulse generator (Digitimer Stimulator DS9A, Welwyn Garden City, UK). The applied voltages were around 30 V, resulting in field strengths of around 10 kV/cm due to the short distance between the electrodes. Both the voltages and field strengths reported are nominal and not corrected for electrochemical reactions and the electrode-solution voltage drop.

Liposome Preparation

Multilamellar liposomes made from L-α-phosphatidylcholine (PC) and soybean lecithin (SBL) were obtained in high yield using a rotary evaporation method[17]. Lipids where purchased from Sigma-Aldrich, Sweden. Typically, 4 μl of a 0.1 M stock solution of lipid in chloroform, 40 μl methanol and 178 μl chloroform were added, together with intracellular buffer (pH 7.4), to a 25 ml round bottle flask. The intracellular buffer consisted of 135 mM KCl, 5 mM NaCl, 20 mM Hepes, 1.5 mM MgCl2 and 10 mM glucose. The organic solvents were rota-evaporated to produce an opaque buffer suspension of liposomes. Occasionally, the membrane of the liposome was stained with the membrane fluorescent dyes DiO (3,3'-dioctadecyloxacarbocyanine perchlorate) and DiI (1,1'-dioctadecyl-3,3,3',3'-tetramethylindocarbocyanine perchlorate) obtained from Molecular Probes Europe BV, The Netherlands.

Cell Electrofusion

A fusion chip with two chambers connected by a ~3 mm long capillary was used. One droplet of red blood cells (RBCs) in iso-osmolar KPi buffer (5 mM Tris, 30 mM K3PO4, 30 mM KH2PO4, 0.5 mM EDTA, 1 mM MgSO4, Milli-Q water, pH adjusted to 7.4 with H2SO4) were added to one or both chambers containing fusion buffer. The electrofusion protocol was similar to liposome electrofusions with the following exceptions. The fusion buffer was a slightly hypo-osmotic KPi buffer (3.9 mM Tris, 23 mM K3PO4, 23 mM KH2PO4, 0.39 mM EDTA and 0.78 mM MgSO4). The applied voltage was 10–12 V, which corresponds to an electrical field of approximately 2–3 kV/cm. The pulse duration was 20 μs. The conductivity of the electrofusion buffer was 9 mS/cm.

RBC-Preparation

Whole blood was obtained from a healthy donor and stored in CPD solution, Maco Pharma, France (citric acid monohydrate 3.27 g, sodiumcitrate dihydrate 26.3 g, sodium dihydrogenphosphate dihydrate 2.51 g, glucose monohydrate 25.5 g, Distilled water 1 L). The blood was donated 2–12 days prior to the experiments. Before fusion experiments, blood was transferred to an iso-osmolar KPi buffer, and centrifuged at 2500 rpm for 10 minutes at room temperature. The buffy coat was removed and cells where resuspended in iso-osmolar KPi buffer and centrifuged again at 2500 rpm. Residual buffy coat was removed and RBCs were suspended in iso-osmolar KPi. Cells were kept at room temperature for no more than 7 hours.

RESULTS AND DISCUSSION

Liposome Transport and Fusion

Figure 1:
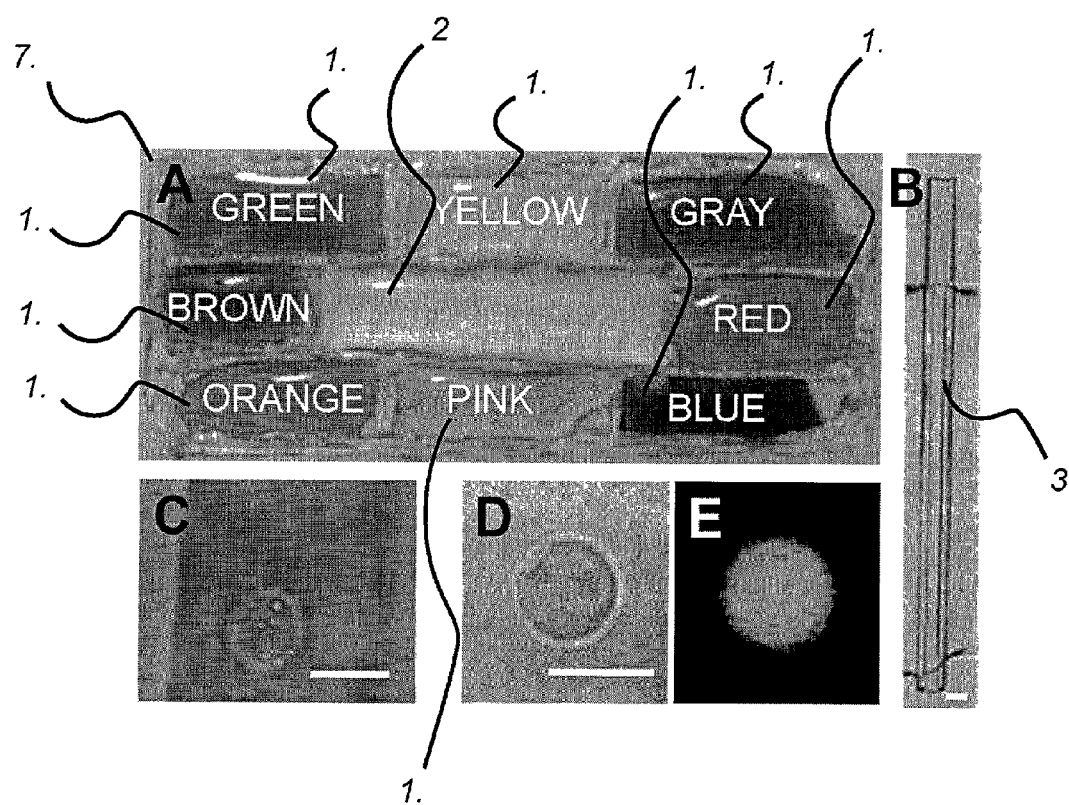
FIG. 1. (A) Stereomicrograph of a 9-well electroporation/electrofusion device. To illustrate the separation of the chambers, the wells are filled with different dyes. The dyes are water-based colors from fiber pens (Carioca). Sample containers 1, are connected to a central fusion/electroporation chamber 2, through microchannels 3. The volume of the sample containers ranged from 200 μl to 500 μl, depending on the size of the containers. Since the device is printed in close to its natural actual size (24*60 mm), the connecting capillaries (o.d. 30–50 μm) can not be seen. In the central fusion container, which is filled with a buffer solution, fusion of the selected liposomes and cells are performed with carbon fiber microelectrodes (not shown). The positioning of the electrodes is performed with high-graduation micromanipulators.

A prototype microfluidic device for combinatorial design of liposomes is shown in FIG. 1A. Liposomes were manipulated and transported by using an optical-trapping [Ashkin, A.; Dziedzic, J. M.; Bjorkholm, J. E.; Chu, S. Opt. Lett. 1986, 11, 288–290; Block, S. M. Noninvasive techniques in cell biology, Modern Cell Biology. Alan R. Liss: New York, 1990, Chapter 15] system and translation of the microscope stage (FIG. 2). The range of sizes of multilamellar liposomes that could be handled with this system was between a few hundreds of nanometers up to tens of micrometers in diameter. This corresponds well to the range of liposome sizes obtained by the preparation method used [Moscho, A.; Orwar, O.; Chiu, D. T.; Modi, B. P.; Zare, R. N. Proc. Natl. Acad. Sci. U.S.A. 1996, 93, 11443–11447]. Manipulations were performed as follows; first, different preparations of liposomes, each with known and well-defined phospholipid composition and contents were placed in individual sample containers-one type of liposome for each container. Second, single liposomes were selected from the different sample containers and transported through 10-to-30 μm i.d. microchannels (FIGS. 1B–C) into the fusion container by optical trapping. In the fusion container, selected liposomes were fused by the application of a short-duration voltage pulse through a pair of 5 μm-diameter solid carbon fiber microelectrodes controlled by high-graduation micromanipulators [Chiu, D. T.; Wilson, C. F.; Ryttsén, F.; Strömberg, A.; Farre, C.; Karlsson, A.; Nordholm, S.; Gaggar, A.; Modi, B. P.; Moscho, A.; Garza-López, R. A.; Orwar, O.; Zare, R. N. Science 1999, 283, 1892–1895]. In addition to the device presented here, several other chip designs are available for cell selection, and cell sorting where cells are propagated in narrow channels by optical trapping/device translation [Morishima, K.; Arai, F.; Fukuda, T.; Matsuura, H.; Yoshikawa, K. Anal. Chim. Acta 1998, 365(1–3), 273–278] or electrophoresis [Li, P. C. D.;Harrison, D. J. Anal. Chem. 1997, 69, 1564–1568; Fu, A. Y.; Spence, C.; Scherer, A.; Arnold, F. H.; Quake, S. R. Nat. Biotechnol. 1999, 17, 1109–1111]. Electrophoresis- and electroosmosis-driven systems are attractive, in particular, for transport of flaccid unilamellar liposomes that sometimes are difficult to trap with optical tweezers. They do, however, not offer as high positional precision as optical tweezers, and alignment of a liposome pair for fusion might be more difficult.

The partitioning between the different sample chambers and the fusion chamber serves two purposes. First, liposomes with different composition can be stored without mixing. Second, liposomes are purified and isolated from the external solution in the sample chamber during transport to the fusion chamber. This is crucial for performing fusion-induced chemical reactions, which are to take place inside liposomes. Because of the nature of most liposome preparation protocols, the extra-liposomal solution will contain the same components as entrapped or expressed inside the liposomes, and consequently reactions will be initiated in the extra-liposomal solution as soon as these are mixed. The dimension of the microchannels is small enough (10-to-30 μm i.d., total volume about 100 nL, compared to the sample containers which contains about 200–500 μl) to act as a barrier for free diffusion of unwanted or unencapsulated molecules into the fusion reservoir. Provided that the fusion chamber contains an iso-osmotic buffer, the liposomes will not be subjected to any damaging osmotic gradients. To further facilitate the purification and isolation of liposomes from their surrounding solution, a hydrodynamic flow from the fusion container into the sample containers was produced by rising the surface level in the fusion container above the surface level in the sample containers. As long as the flow was reasonably low, the optical trapping force was sufficiently strong to keep a liposome firmly trapped during transportation. The efficiency of the exchange of extra-liposomal solution is exemplified in FIG. 1D-E, where a fluorescein-containing (10 μM) liposome was transferred from its storage depot to the fusion chamber. The background fluorescence from the surrounding solution was decreased more than 100-fold after transfer.

Combinatorial Fusion

By employing a combinatorial fusion scheme with liposomes made from well-defined components, and different intra-liposomal contents as basic building blocks, product liposomes of complex membrane compositions and contents can be created. The fusions can be made sequentially to follow a specific order of a complex reaction. This is described schematically in FIG. 7 where four liposomes with different membrane structures, and different contents are fused pair-wise. A quite large number of different product liposomes can be obtained from a few starting liposomes or cells through combinatorial pair-wise fusion. From four starting liposomes, as in the example above, eleven different product liposomes can be obtained. If the number of starting liposomes are increased to twenty, more than one million hybrid liposomes could theoretically be obtained via >1.7 billion discrete pathways [The formula $2^n-n-1$, where n is the number of starting liposomes, is used to calculate the number of different liposomes that can be obtained. The number of different pathways that are available to reach the hybrid products can be found from the general expression $$\sum_{k=2}^{n} \binom{n}{k}(2^{k-1}-1)$$

where n is the number of starting liposomes and k is the number of starting liposomes in the intermediate products]. A significant advantage in using liposome fusion for initiation of chemical reactions compared to microinjection methods [Bucher, P.; Fischer, A.; Luisi, P. L.; Oberholzer, T.; Walde, P. Langmuir 1998, 14(10), 2712–2721], is that one or several reaction systems can be combined at the same time as the lipid composition is altered in the reaction liposome.

Multiple sequential fusions where liposomes with different dyes incorporated in their membranes were fused and is shown in FIG. 8A-H. The first fusion (A-D) involves a liposome with no membrane dye incorporated and a green fluorescent liposome with DiO (3,3'-dioctadecyloxacarbocyanine perchlorate) incorporated in the membrane. The product liposome, shown in D, was then fused with a red fluorescent liposome with DiI (1,1'-dioctadecyl-3,3,3',3'-tetramethylindocarbocyanine perchlorate) incorporated in the membrane (E-H). The fluorescent membrane dyes were evenly distributed after each fusion as shown in the figure. However, there have been reports that different lipid bilayer phases coexists within the same unilamellar liposome, visualized by the uneven distribution of fluorescently tagged phospholipids [Korlach, J. Schwille, P., Webb, W. W., Feigenson, G. W., Proc. Natl. Acad. Sci, U.S.A., 1999, 96, 8461–8466].

According to the invention it is also possible to alter the lipid and membrane protein composition of single liposomes by fusing liposomes of different lipid and protein content. For example, phosphatidyl choline (PC) liposomes were fused with PC—soybean lecithin liposomes, resulting in an overall increase in the PC content and PC liposomes with membrane proteins could be fused with PC liposomes devoid of membrane proteins (not shown). Liposomes obtained by the preparation method used here are size-distributed between tens of nanometers up to several micrometers in diameter. Thus, by selecting the sizes of fusion partners, careful and quantitative combination of different membrane components or interior contents at any predetermined ratio could be achieved with liposomes between ~3–30 μm in diameter. Although the above description centered around liposomes, a combinatorial library of fused cells can similarly be generated using the method described here.

Cell Transport and Fusion

The microfluidic-fusion device can be advantageous for single cell-cell electrofusions in several aspects, in addition to the fact that the identities of the different fusion partners are always established. For example, cells can be kept in a physiological buffer until fused in a low conductive-low osmotic buffer. Correspondingly, fused cells can be moved to a container with postfusion medium for recovery. To demonstrate the applicability of cell fusions in the microchannel device, red blood cells were transported and fused as shown in FIG. 9. Fusions were achieved between one transported, and one non-transported cell as well as between two transported cells. These fusions were performed in a high-conductivity medium (9 mS/cm), and therefore dielectrophoresis (the application of an alternating field of usually MHz frequencies which causes cells to come in close contact to each other due to charge separation within the cell) was not applicable. This was not a problem since close cell contact could be achieved mechanically [Kramer, I., Vienken, K., Vienken, J., Zimmermann, U., Biochim. Biophys. Acta 1984, 772, 407–410] by using the microelectrodes. The RBCs did not show any signs of damage due to the optical trapping, and non-damaging optical trapping of RBCs has been reported earlier [Ashkin, A., Dziedzic, J. M., Yamane, T., Nature, 1987, 330, 769–771]. The final fused cell is shown in (C). The grayish line that seems to divide the fused cell into two halves is the waist of the dumbbell shape of the fused cell. As the cytoskeleton is intact inside the RBCs, total rounding up of the fused cell is not achieved.

We claim:

1. A method for electromanipulation of at least one cell or cell-like structure having cell-like membranes, comprising the following consecutive steps:

(a) at least one cell or cell-like structure is transported from one or more sample containers located on a chip through at least one microchannel located on said chip into a chamber located on said chip, wherein said chamber contains at least one microelectrode connected to a voltage generator, and wherein said microchannel provides a fluid contact between the sample containers, (b) either said at least one cell or cell-like structure is placed or aligned close to said at least one electrode, or said at least one microelectrode is placed or aligned close to said at least one cell or cell-like structure in said chamber, (c) an electrical field is applied and focused on said at least one cell or cell-like structures, said electrical field being of a strength sufficient to obtain pore-formation in said at least one cell or cell-like structure or sufficient to obtain fusion of said at least one cell or cell-like structure with another cell or cell-like structures in said chamber.

2. The method of claim 1, wherein step (a) wherein the transport of said at least one cell or cell-like structures inside said microchannels is performed by optical trapping in combination with device translation.

3. The method of claim 1, wherein at least one agent is delivered through said pore formed in step (c) into said at least one cell or cell-like structure.

4. The method of claim 3, wherein said at least one agent is delivered through said pore and into said cell or cell-like structure followed by delivery of at least one other agent through said pore and into said cell or cell-like structure cell structure, wherein the deliveries of the different agents are performed in a sequential manner.

5. The method of claim 3, wherein said at least one agent is delivered through said pore and into said cell or cell-like structure followed by delivery of at least one other agent through said pore and into said cell or cell-like structure cell structure, wherein the deliveries of the different agents are performed in a parallel manner.

6. The method of claim 4, wherein the deliveries of the different agents are performed in a combinatorial manner.

7. The method of claim 3, wherein said at least one agent is delivered through said pore and into said cell or cell-like structure followed by delivery of at least one other agent through said pore and into said cell or cell-like structure cell structure, wherein the deliveries of the different agents are performed in a combinatorial manner.

8. The method of claim 4, wherein said agent is selected from the group consisting of pharmaceutically active compounds, electrolytes, substances that activate receptors on the cell plasma membrane, agents that affects intracellular chemistry, agents that affects cellular physics, genes, gene analogs, RNA, RNA analogs, DNA, DNA analogs, colloidal particles, receptors, receptor ligands, receptor antagonists, receptor blockers, enzymes, enzyme substrates, enzyme inhibitors, enzyme modulators, proteins, protein analogs, amino acids, amino acid analogs, peptides, peptide analogs, metabolites, metabolite analogs, oligonucleotides, oligonucleotide analogs, antigens, antigen analogs, haptens, hapten analogs, antibodies, antibody analogs, organelles, organelle analogs, cell nuclei, bacteria, viruses, gametes, inorganic ions, metal ions, metal clusters, polymers, and any combinations thereof.

9. The method of claim 5, wherein said agent is selected from the group consisting of pharmaceutically active compounds, electrolytes, substances that activate receptors on the cell plasma membrane, agents that affects intracellular chemistry, agents that affects cellular physics, genes, gene analogs, RNA, RNA analogs, DNA, DNA analogs, colloidal particles, receptors, receptor ligands, receptor antagonists, receptor blockers, enzymes, enzyme substrates, enzyme inhibitors, enzyme modulators, proteins, protein analogs, amino acids, amino acid analogs, peptides, peptide analogs, metabolites, metabolite analogs, oligonucleotides, oligonucleotide analogs, antigens, antigen analogs, haptens, hapten analogs, antibodies, antibody analogs, organelles, organelle analogs, cell nuclei, bacteria, viruses, gametes, inorganic ions, metal ions, metal clusters, polymers, and any combinations thereof.

10. The method of claim 1 wherein step (a) wherein the transport of said at least one cell or cell-like structures inside said microchannels is performed by electrophoresis.

11. The method of claim 1, wherein the transport of said at least one cell or cell-like structures inside said microchannels is performed by electroendoosmotic flows.

12. The method of claim 1, wherein the transport of said at least one cell or cell-like structures inside said microchannels is performed by dielectrophoresis.

13. The method of claim 1, wherein the transport of said at least one cell or cell-like structures inside said microchannels is performed by gravitational liquid flow.

14. The method of claim 1, wherein the transport of said at least one cell or cell-like structures inside said microchannels is performed by pressurized liquid flow.

15. The method of claim 1, wherein steps (a)–(c) are repeated until a desired number of cell or cell-like structures have been fused together.

16. The method of claim 1 comprising a further step (d) performed after step (c), wherein electroporated or fused said at least one cell or cell-like structure is transported to a storage container in fluid contact with said chamber.

17. The method of claim 1, wherein said at least one microelectrode is positioned in step (b) by means of a microscope, a micropositioner or a stereotactic device.

18. The method of claim 1, wherein said microelectrode being sufficiently small to enable selective fusion of said cells or cell-like structures.

19. The method of claim 1, wherein two microelectrodes are used in step (c) and said two microelectrodes are sufficiently small to enable selective fusion of said cells or cell-like structures.

20. The method of claim 1, wherein one microelectrode is movably mounted on a microchip, said microelectrode being sufficiently small to enable selective fusion of said cells or cell-like structures.

21. The method of claim 20, wherein said microchip is the same chip on which the container, the microchannel and the chamber are located.

22. The method of claim 1, wherein several microelectrodes individually movably mounted on a microchip, said microelectrodes being sufficiently small to enable selective fusion of said cells or cell-like structures.

23. The method of claim 1, wherein said microchip is the same chip on which the container, the microchannel and the chamber are located.

24. The method of claim 1, wherein at least one of the at least one electrodes is a hollow microelectrode.

25. The method of claim 24, wherein said hollow microelectrode is located on the same chip on which the container, the microchannel and the chamber are located.

26. The method of claim 24, wherein said hollow microelectrode is filled with an electrolyte and wherein at least one agent is delivered by electroendoosmosis, electrophoresis or Poiseuille flow through the microelectrode into the fusion container.

27. The method of claim 25, wherein said hollow microelectrode is filled with an electrolyte and wherein at least on agent is delivered by electroendoosmosis, electrophoresis or Poiseuille flow through the microelectrode into the fusion container.

28. The method of claim 1, wherein the outer diameter of said at least one microelectrode is 0.05–100 µm.

29. The method of claim 1, wherein the outer diameter of said at least one electrode is 1–50 µm.

30. The method of claim 1 wherein said at least one microelectrode provided in step (c) also is used for positioning of said at least cells or cell-like structures in step (b).

31. The method of claim 1, wherein said cells or cell-like structures independently are selected from the group consisting of cells, liposomes, proteoliposomes, synthetic vesicles, egg cells, enucleated egg cells, sperm cells at any developmental stage and plant proteoplasts.

32. The method of claim 1, wherein said at cell-like structures are liposomes.

33. The method of claim 1, wherein said at least one cell or cell-like structure is a cell.

34. The method of claim 1, wherein at least one of said cells or cell-like structures is a liposome and at least one of said cells or cell-like structures is a cell.

35. The method of claim 1, wherein the cell or cell-like structures to be transported in step (a) is selected from a library of cells or cell-like structures in a combinatioral manner.

36. The method of claim 1, wherein the electrical field in step (d) is applied by use of a low-voltage pulse-generator.

37. The method of claim 1, wherein the sample containers containing the cells or cell-like structures also contains a buffer.

38. The method of claim 1, wherein said at least one microelectrode provided in step (c) is used for electroporation of said cells or cell-like structures between steps (a) and (b).

39. The method of claim 1, wherein at least one of said cells or cell-like structures is exposed to a dielectrophoretic field in a buffer prior to step (b).

40. The method of claim 1, wherein at least one of said cells or cell-like structures is treated with a fusogenic or other agent that promotes close cell-cell contacts prior to step (b).

41. An apparatus for electromanipulation of at least one cell or cell-like structure having cell-like membranes, said apparatus comprising one or more sample containers for said cell or cell-like structure in fluid contact through at least one microchannel with a fusion chamber, optical trapping means for transport of individual cells or cell-like structures through said at least one microchannel into the fusion chamber, and at least one microelectrode connected to a voltage generator for providing a focused electrical field in the fusion chamber, wherein said sample container, said microchannel and said fusion chamber are placed on a chip.

42. The apparatus of claim 41, wherein said at least one microelectrode is integrated on said chip.

43. The apparatus of claim 41, further comprising at least one microscope, at least one micropositioner or at least one stereotactic device for positioning of said at least one microelectrode.

44. The apparatus of claim 41, comprising only one microelectrode.

45. The apparatus of claim 41, having two microelectrodes.

46. The apparatus of claim 41, wherein the microelectrode is movably mounted on a microchip.

47. The apparatus of claim 41, having several microelectrodes individually movably mounted on a microchip.

48. The apparatus of claim 41, wherein at least one microelectrode is hollow.

49. The apparatus of claim 48, wherein said at least one hollow microelectrode is filled with an electrolyte.

50. The apparatus of claim 41, wherein the outer diameter of said at least one microelectrode is 0.05–100 µm.

51. The apparatus of claim 41, wherein the outer diameter of said at least one electrode is 1–50 µm.

52. The apparatus of claim 41, wherein said voltage generator is a low-voltage pulse-generator.

53. The apparatus of claim 41, wherein the sample containers contains a buffer.

54. The method of claim 1, wherein the electromanipulation of at least one cell is used for in vitro fertilization.

55. The method of claim 1, wherein the electromanipulation of at least one cell is for in vitro fertilization and comprising using the apparatus according to claim 41.

56. The method of claim 1, wherein the electromanipulation of at least one cell is used for cloning.

57. The method of claim 1, wherein the electromanipulation of at least one cell is used for cloning using the apparatus according to claim 41.

58. The method of claim 1, wherein the electromanipulation of at least one cell is for cell transfection.

59. The method of claim 1, wherein the electromanipulation of at least one cell is used for cell transfection using the apparatus according to claim 41.

60. The method of claim 1, wherein the electromanipulation of at least one-cell is for the production of monoclonal antibodies.

61. The method of claim 1, wherein the electromanipulation of at least one cell is used for the production of monoclonal antibodies using the apparatus according to claim 41.

62. The method of claim 1, wherein the electromanipulation of at least one cell is for the preparation of a hybridoma.

63. The method of claim 1, wherein the electromanipulation of at least one cell is used for the preparation of a hybridoma using the apparatus according to claim 41.

64. The method of claim 1, wherein the electromanipulation of at least one cell is for the manipulation of a cellular membrane.

65. The method of claim 1, wherein the electromanipulation of at least one cell is used for the manipulation of a cellular membrane using the apparatus according to claim 41.

66. The method of claim 1, wherein the electromanipulation of at least one cell is for the delivery of a well-defined volume of a substance to a cell 67. The method of claim 1, wherein the electromanipulation of at least one cell is used for the delivery of a well-defined volume of a substance to a cell using the apparatus according to claim 41.

68. A The method of claim 1, wherein the electromanipulation of at least one cell is used for the delivery of a pharmaceutically active substance to a cell.

69. The method of claim 1, wherein the electromanipulation of at least one cell is used for the delivery of a pharmaceutically active substance to a cell using the apparatus according to claim 41.

* * * * *